United States Patent [19]
Chen

[11] Patent Number: 4,722,346
[45] Date of Patent: * Feb. 2, 1988

[54] STAND-OFF DEVICE WITH SPECIAL FLUID

[75] Inventor: James N. Chen, Chelmsford, Mass.

[73] Assignee: Hewlett-Packard Company, Palo Alto, Calif.

[*] Notice: The portion of the term of this patent subsequent to Aug. 5, 2003 has been disclaimed.

[21] Appl. No.: 843,363

[22] Filed: Mar. 24, 1986

Related U.S. Application Data

[63] Continuation of Ser. No. 562,307, Dec. 16, 1983, Pat. No. 4,603,701.

[51] Int. Cl.$^4$ ............................................. A61B 10/00
[52] U.S. Cl. ........................................ 128/660; 73/644
[58] Field of Search .............................. 128/660–663; 73/644

[56] References Cited

U.S. PATENT DOCUMENTS

| | | | |
|---|---|---|---|
| 3,603,303 | 9/1971 | Stouffer | 128/660 |
| 4,002,221 | 1/1977 | Buchalter | 73/644 |
| 4,059,098 | 11/1977 | Murdock | 128/660 |
| 4,184,094 | 1/1980 | Kupel | 128/660 |
| 4,185,501 | 1/1980 | Proudian et al. | 128/660 |
| 4,279,167 | 7/1981 | Erb et al. | 73/644 |

OTHER PUBLICATIONS

Paulaskas et al, "Ultrasonic Investigation of the Three Component Systems Dioxan-Water-RbCl (or CsCl)" Ul'Trazvuk No. 9, 1977, pp. 67–69.

Abaraviciute et al, "Ultra Acoustical Studies of Ethanol-Water-Cesium Chloride, Barium Chloride, or Lanthanum Chloride Systems," Liestr aukstuju mokyklu darbei ultragarsas nauch tr vyssh ucheb zavedenii litssr Ul'trazvuk (9) 70–3 1977.

Smirnov et al., "Ultrasound Velocity and Adiabatic Compressibility in Cesium Halide Binary Fused Mixtures" deposited Doc., Viniti 7046-73, 15 pages, 1973.

*Primary Examiner*—Kyle L. Howell
*Assistant Examiner*—Ruth S. Smith
*Attorney, Agent, or Firm*—Donald N. Timbie

[57] ABSTRACT

A stand-off device for use with acoustic transducers is described in which a chamber having a diaphragm portion contains liquid, the ratio of the acoustic impedance of said diaphragm to the acoustic impedance of soft body tissue and the ratio of the acoustic impedance of said liquid to the acoustic impedance of said diaphragm being whole numbers or fractions, and said diaphragm being of such thickness that reflections from its diaphragm/body interface, when it is held against the body of a patient, and its liquid/diaphragm interface tends to cancel each other.

4 Claims, 4 Drawing Figures

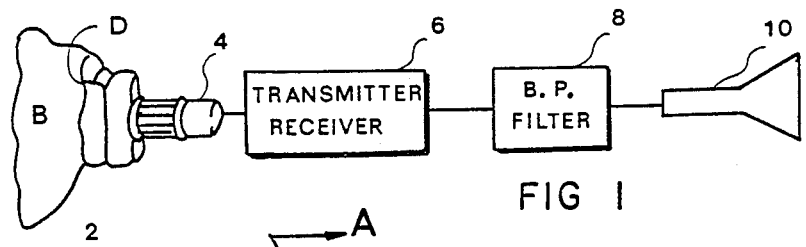
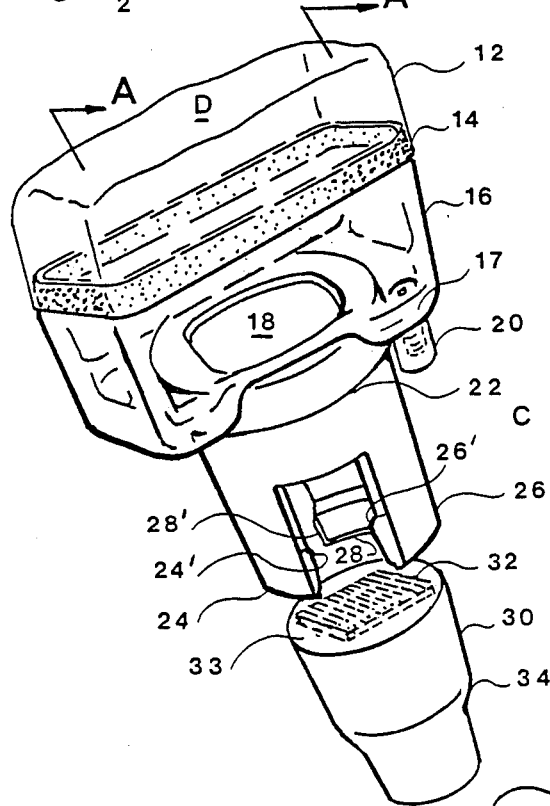
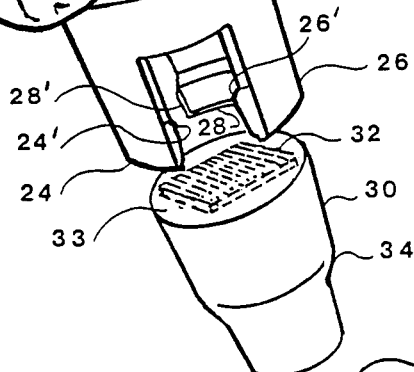
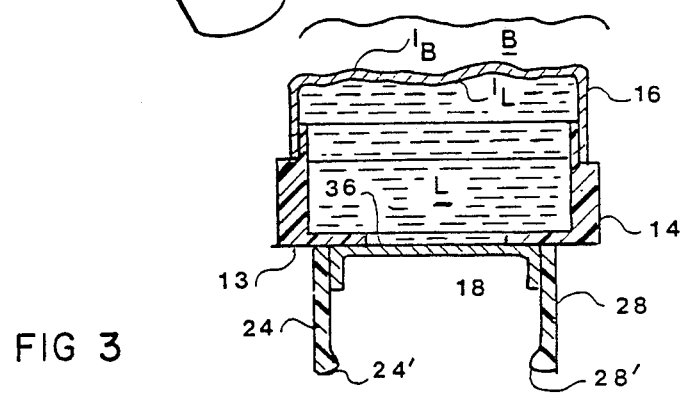

STAND-OFF DEVICE WITH SPECIAL FLUID

CROSS REFERENCE TO RELATED APPLICATION

This is a continuation of application Ser. No. 06/562,307, filed 12/16/83 now U.S. Pat. No. 4,603,701.

BACKGROUND OF THE INVENTION

In some ultrasound systems used for forming images of the interior of a patient's body, pulses of ultrasonic waves are directed into the body from a transducer held against it and reflection of these waves from structures within the body causes the transducer to produce corresponding electrical waves that are used to form the desired image. For various reasons, structures near the surface of the body and therefore near the transducer are not sharply focussed so that when such structures are of interest, it has been customary to place them within an area of better focus by inserting a stand-off device between the transducer and the patient's body. This also increases the field of view around these structures so that they can be more easily identified. In order to provide good acoustic coupling, standoff devices have been comprised of a liquid-filled chamber having a diaphragm portion at one end, which is placed in initimate contact with the body, and a membrane portion at the other end, which is placed in intimate contact with the transducer. In some cases, no membrane is used and the transducer is placed in intimate contact with the liquid in the chamber.

A major problem with stand-off devices is that the quality of the image at one or more ranges is impaired by the low amplitude reflections of the ultrasonic waves of the pulses at the liquid/diaphragm and diaphragm/body interfaces. These reflections arrive at the transducer at about the same time as waves reflected from body structures that are close to the diaphragm, thereby deteriorating their image, and yet the attainment of a better image of these structures was the reason for using the stand-off device. It is also possible that the low amplitude waves reflected from the interfaces will be reflected by the transducer and again reflected at the liquid/diaphragm and diaphragm/body interfaces so as to reduce the quality of images of structures located in the body a distance from the diaphragm that is the same as the distance between the diaphragm and the transducer.

BRIEF SUMMARY OF THE INVENTION

In accordance with this invention, the thickness of the diaphragm, its acoustic impednace, and the acoustic impedance of the liquid are such that when the diaphragm is held against soft body tissue, the waves respectively reflected at the liquid/diaphragm and diaphragm/body interfaces have phase and amplitude relationships that tend to cancel each other and thereby reduce the deleterious effect that they might have on the image.

When waves generated by the transducer pass through the liquid and impinge on the liquid/diaphragm interface, a portion of their energy is reflected in the form of waves having an amplitude equal to a small fraction of the amplitude of the impinging wave determined by the expression $$(Z_D - Z_L)/(Z_D + Z_L)$$

in which $Z_D$ is the acoustic impedance of the diaphragm material and $Z_L$ is the acoustic impednace of the liquid. This fraction is the reflection coefficient of the liquid/diaphragm interface.

Because of the reflected energy, the waves entering the diaphragm have an amplitude that is less than that of the waves that impinged on the liquid/diaphragm interface; and these are attenuated as they pass through the diaphragm. When they impinge on the diaphragm/body interface, a portion of their energy is reflected in the form of waves having an amplitude equal to a small fraction of the amplitude of the impinging wave determined by the expression $$(Z_B - Z_D)/(Z_B + Z_D)$$

in which $Z_B$ is the acoustic impedance of soft body tissue. This fraction is the reflection coefficient of the diaphragm/body interface.

If the thickness of the diaphragm is one-quarter of the wavelength of the wave, the waves reflected back toward the transducer at the liquid/diaphragm interface and the diaphragm/body interface will be 180 degrees out of phase so that they will tend to cancel each other. To compensate the above-mentioned reflection and attenuation effect, the reflection coefficient of the liquid-diaphragm interface is made slightly smaller than the reflection coefficient of the diaphragm/body interface. Under these conditions, the reflections of pulse energy at the two interfaces would arrive at the transducer in the form of a wave having two oppositely poled half-cycles separated by a portion of zero amplitude. A band pass filter can be placed in the path of the electrical signals generated by the transducer so as to severely reduce these half-cycles and pass the electrical signals corresponding to the waves reflected by structures within the body.

It is to be noted that if $Z_D$ is greater than $Z_B$, $Z_L$ will have to be greater than $Z_D$ if both reflection coefficients are to be negative; and if $Z_D$ is less than $Z_B$, $Z_L$ will have to be less than $Z_D$ if both reflection coefficients are to be positive.

As a practical matter, the attenuation of the diaphragm may be ignored because the diaphragm is thin; and if the reduction in the amplitude of the waves entering the diaphragm because of the reflection at the liquid/diaphragm interface is also ignored because it is so small, it can be said that the reflection coefficients will be equal and have the same sign if $Z_B/Z_D$ equals $Z_D/Z_L$. If the reflection coefficients are to be positive, $Z_B$ will be greater than $Z_D$ and $Z_D$ will be greater than $Z_L$ so that both ratios will be the same value greater than one; and if the reflection coefficients are to be negative, $Z_B$ will be less than $Z_D$ and $Z_D$ will be less than $Z_L$ so that the ratios equal the same fraction.

In addition to making the reflected waves tend to cancel each other in the manner just described, this invention includes the use of diaphragm material that is flexible and tough and which has an acoustic impedance $Z_D$ that is greater than $Z_B$ so that $Z_L$ must be greater than $Z_D$. It furthermore includes solutions of the salt Cesium Chloride or thallous format so as to attain the higher value of $Z_L$ required.

BRIEF DESCRIPTION OF THE DRAWINGS

FIG. 1 illustrates the major components of an ultrasound system;

FIG. 2A is a transparent projection view of a standoff device;

FIG. 2B shows a transducer that will be coupled to the stand-off device of FIG. 2A; and FIG. 3 is a section AA of FIG. 2A.

DETAILED DESCRIPTION OF THE INVENTION

The acoustic impedance of body tissue is generally estimated to be about 1.58 megrayls, and since most materials that are otherwise satisfactory for the diaphragm have a higher acoustic impedance, the first alternative mentioned above would normally be used so that the acoustic impedance of the liquid would have to exceed that of the diaphragm. For various reasons set forth below, polyethylene having an acoustic impedance of 1.8 megrayls was chosen for the diaphragm so that it was necessary to find a liquid having an acoustic impedance of close to 2.05. This was difficult to do and is essentially satisfied by a preferred mixture for this particular application that has the following proportions by weight:

cesium chloride: 15.0%
glycerin: 20.6%
ethylene glycol: 41.2%
propylene glycol: 23.2%

Of these constituents, cesium chloride has been found to be the most critical because it has the high density necessary to increase the acoustic impedance of a liquid in which it is dissolved. The percentages of the other constituents can be varied more than the percentage of cesium chloride without appreciably changing the acoustic impednace of the mixture. In fact, other liquids may be substituted for the other three constituents if the proportions are changed. It should be kept in mind that a selection of a diaphragm material having a greater acoustic impedance than 1.8 megrayls would require a greater proportion of cesium chloride and, conversely, that selection of a diaphragm material having a lesser acoustic impedance than 1.8 megrayls but larger than 1.6 megrayls would require a smaller proportion of cesium chloride.

Furthermore, if the diaphragm significantly attenuates the acoustic waves passing through it, the waves reflected from the diaphragm/body interface will have an amplitude less than the amplitude of the acoustic waves reflected from the liquid/diaphragm interface so that complete cancellation of the waves in the central portions of the reflected pulses does not occur. In this event, the acoustic impedance of the liquid can be decreased by use of a lesser portion of cesium chloride so as to reduce the amplitude of the waves reflected at the liquid/diaphragm interface to that of the waves reflected from the diaphragm/body interface and produce perfect cancellation of the central portions of the reflected pulses.

In addition to having an appropriate acoustic impedance, the liquid should have an acoustic velocity very close to the velocity of 1.6 of the soft tissue as this will make the interpretation of the image easier. It should also have as low a viscosity as possible so as to minimize the attenuation of the acoustic pulses passing through it. An attenuation of about 1 db/cm at 5MHz would be satisfactory.

FIG. 1 illustrates an ultrasound system having a stand-off device 2 interposed between a body B being examined and a transducer 4. A transceiver 6 is coupled to the transducer 4 so as to cause it to transmit ultrasonic waves. The transceiver 6 also receives the electrical signals produced by the transducer 4 in response to the impingement thereon of reflections of the transmitted waves and produces signals from which an image can be formed. These signals are coupled via a bandpass filter 8 to a cathode ray tube 10 or other image-forming means.

The stand-off device 2 is a chamber containing liquid that causes the transducer 4 to stand off from the body B so that certain portions of the body B are in a region of better focus. If the system is of the sector-scanning type, the stand-off device 2 also causes those structures near the surface of the body B to be well within the sector where they are surrounded by enough other structures to simplify identification.

Reference is now made to FIG. 2A for a description of the construction of one embodiment of a stand-off device that may incorporate the invention. This embodiment is similar to that which is the subject of a joint invention of myself and Thaddeus G. Minior, the patent application for which is filed concurrently herewith. In order to simplify the drawing, all parts of the device are shown as being transparent, but certain parts could just as well be opaque. The chamber of the stand-off device is formed in part by diaphragm D that is made of pliant material such as polyethylene in the form of a hollow rectangular box 12 with one side open. The inner edge of this open side is adhered, as indicated at 14, to the outer edge of an open side of a hollow rectangular box 16 that is made of rigid material. The bottom 17 of the box 16, which is opposite its open side, is provided with an opening 18 and a filling port 20 through which liquid can be introduced into the interior of the chamber formed by the hollow boxes 12 and 16. A clip C that is mounted on the outside of the bottom 17 has an opening in its top 22 that is in registration with the opening 18 in the bottom 17 of the box 16. When a transducer is mounted within the clip C so as to fill the opening 18, the chamber is completely enclosed. Resilient fingers 24, 26 and 28 that are longitudinal portions of an annulus and perpendicular to the bottom 17 of the box 16 are respectively provided with inwardly extending curved ridges 24', 26' and 28'. The fingers 24, 26 and 28 are centered 90 degrees apart so that there is a fourth finger, not visible in this view, that is opposite the finger 26.

FIG. 2B shows the exterior of a cylindrical transducer 30 having an array 32 of parallel crystals protruding from one end and covered by a lens 33. The outer diameter of the transducer 30 is such that it can be axially inserted within the resilient fingers 24, 26 and 28 so as to position the array 32 in the opening 18 in the bottom 17 of the box 16. An annular step 34 on the outside of the transducer 30 is positioned so as to exert radially outward forces on the ridges 24', 26' and 28' respectively at the inner ends of the fingers 24, 26 and 28 so as to push the fingers outwardly as the transducer 30 is being inserted. When the transducer 30 reaches its final position, the step 34 slides above the ridges 24', 26' and 28' and the fingers move inwardly so as to hold the transducer 30 firmly in place.

If the top 22 of the clip C is sealed to the bottom 17 of the box 16, liquid can be introduced into the interior of the boxes 12 and 16 that form the chamber via the filling port 20, in which event the liquid is coupled to the array 32 by contact with the lens 33. Instead of coupling the liquid to the transducer 30 in this manner, a membrane (not shown in FIG. 2A) could be sealed to the bottom 17 of the box 16 so as to be in contact with the lends 33 when the transducer 30 is mounted in the clip C. Such a membrane could be made of pliant material having an acoustic impedance similar to the transducer lens 33 or the liquid.

FIG. 3, which is a cross-section AA of FIG. 2A, further illustrates the structure just described and has, in addition, a membrane 36 that is sealed to the outside of the bottom 17 of the box 16 so as to cover the opening 18 therein. Although not shown in FIG. 3, the filling port 20 would extend through the membrane 36. Most importantly, FIG. 3 shows the liquid L that is introduced into the chamber formed within the boxes 12 and 16 via the filling port 20. As best seen in FIG. 3, the diaphragm/body interface is at $I_B$ and the liquid/diaphragm interface is indicated at $I_L$.

The characteristics of a number of liquid mixtures are set forth in the table below. The percentages of each component refers to its relative weight. As can be seen, the preferred liquid indicated by an asterisk (*) has an acoustic impedance of 2.02 megrayls that is very near to what is required to make the amplitude reflection coefficients at the diaphragm/body and liquid/diaphragm interfaces the same when the body is considered to have an impedance of 1.58 megrayls and the portion of the chamber wall of the diaphragm D that is adjacent the body is made of light density polyethylene having an impedance of 1.8 megrayls. As previously noted, however, a liquid having a different acoustic impedance would be preferable if the body tissue and/or the diaphragm had different impedances than those just indicated. It should also be noted that substances other than one or more of glycerin, ethylene glycol and propylene gylcol could be used, but in accordance with this invention a liquid having an acoustic impedance sufficiently greater than that of any practicable diaphragm so as to reflect acoustic waves at the liquid/diaphragm interface that exhibit any significant degree of cancellation with the acoustic waves reflected at the diaphragm/body interface will have to contain cesium chloride or the solution of some high density salt. Thallous format or iodoform may be used in place of cesium chloride but their toxicity makes them less desirable for stand-off devices that are to be in contact with the human body. Another salt that may be used is Cesium Sulfate.

at the diaphragm/body interface. Furthermore, the attenuation of sound waves should be a minimum and the vapor pressures of the various ingredients should be low so that the fluid will retain its initial characteristics.

The table below sets forth the pertinent characteristics of a number of materials that might be used for the diaphragm.

| Diaphragm Material | Acoustic Impedance | Required Liquid Impedance | Remarks |
| --- | --- | --- | --- |
| natural rubber | 1.74 | 1.92 | a. high vapor leakage rate<br>b. attacked by fluids used as coupling, e.g., mineral oil<br>c. difficult to form sufficiently thin diaphragm |
| neoprene | — | — | |
| polybutadine | 1.73 | 1.89 | if sufficiently flexible, not strong enough |
| polymethyl-pentane | 1.68 | 1.79 | less flexible |
| polyurathine | 2.0 | 2.50 | |
| dimethyl-pentene | 1.8 | 2.05 | |
| *polyethylene | 1.8 | 2.05 | a. easily formed<br>b. low vapor leakage<br>c. very flexible and pliable<br>d. slow crack propagation rate |

*preferred

The reasons why polyethylene is preferred are as follows:
a. It has an acoustic impedance that is close to that of body tissue.
b. It is easily formable into specific shapes.
c. It has low vapor leaking rate and low gas leaking rate compared to many other organic materials.
d. It is flexible and pliable.
e. It has good tear strength and also has a slow crack propagation rate.
f. It is chemically very inert.

In order for the waves respectively reflected at the diaphragm/body and liquid/diaphragm interfaces to be precisely 180 degrees out of phase, the thickness of the diaphragm should be an odd number of quarter-

| | | | | Fluid Mixtures | | | |
| --- | --- | --- | --- | --- | --- | --- | --- |
| Cesium Chloride | Glycerin | Ethylene Glycol | Propylene Glycol | Characteristics | | | |
| | | | | Density | Velocity | Impedance | Attenuation |
| *15.0% | 20.6% | 41.2% | 23.2% | 1.23 | 1.63 | 2.02 | low-1 dB/cm for 5 MHz |
| 15.8% | 15.2% | 41.6% | 27.3% | 1.22 | 1.61 | 1.96 | |
| 11.8% | 16.0% | 43.6% | 28.6% | 1.18 | 1.61 | 1.89 | |
| 14.5% | 19.6% | 53.6% | 12.2% | 1.21 | 1.63 | 1.97 | |
| 13.1% | 17.3% | 47.2% | 22.8% | 1.20 | 1.63 | 1.96 | |
| 57.0% | 28.5% | 14.5% | — | 1.22 | 1.67 | 2.04 | high |
| 20.0% | 27.0% | 53.0% | — | 1.30 | 1.64 | 2.13 | high |
| 16.5% | 22.3% | 61.0% | — | 1.26 | 1.66 | 2.09 | high |
| — | 50.0% | — | 50.0% | 1.14 | 1.65 | 1.88 | high |

*preferred fluid

The reasons for using the four ingredients noted above so as to produce a fluid having a high acoustic impedance are as follows. As previously stated, acoustic impednace is the product of density and acoustic velocity so that a fluid having a high acoustic impedance could be formed with components that have either a high density or a high velocity or both, but the velocity should be kept near the velocity of sound in soft body tissue in order to avoid refraction of the acoustic waves wavelengths of the carrier frequency in the material from which the diaphragm is made. In the preferred material, polyethylene, a quarter-wavelength of a carrier frequency of 5 MHz is 4.0 mils. This thickness was used because it is sufficiently durable and yet flexible enough to conform to the contours of the patient's body as desired. In actual practice, it will be found that the sheet material from the factory varies in thickness and further changes in thickness can result when the box 12 is formed by vacuum-forming or other methods. Omitting the effect of attenuation, which is generally negligible, the variation in thickness in percent of one quarter-wavelength has the effect on the uncancelled energy relative to the energy cancelled for an ideal thickness as indicated in the following table.

| Thickness Variation | Uncancelled Energy |
| --- | --- |
| +50% of quarter-wavelength | 6 db |
| quarter-wavelength | 0 db |
| −20% of quarter-wavelength | 6 db |
| −50% of quarter-wavelength | 13 db |

If the carrier frequency were 10 MHz, the ideal thickness of a diaphragm would be 2 mils, but as this may be too fragile, thicknesses of 6 mils could be used.

With the information set forth herein, one skilled in the art could formulate a liquid having the acoustic impedance required for obtaining highly advantageous cancellation of the acoustic waves reflected from the diaphragm/body and liquid/diaphragm interfaces, low attenuation and the desired acoustic velocity. As one departs from the ideal relationships, the degree of cancellation of the reflected waves is reduced, but more than 6 dB reduction in reflected pressure wave amplitude is considered desirable.

What is claimed is:

1. A stand-off device for coupling an acoustic transducer to a human body having tissue with a given acoustic impedance $Z_B$, comprising:

means defining a chamber having a pliant diaphragm at a side thereof that conforms to the contours of a patient's body, said diaphragm having inner and outer surfaces and having an acoustic impedance $Z_D$ that is between 1.73 and 1.8 megrayls inclusive and a thickness that is within $\mp 50\%$ of a quarter wavelength of an odd integral number of quarter wavelengths of the central frequency transmitted by a transducer with which the stand-off device is to be used, means for coupling another side of said chamber to said transducer, liquid having a given acoustic impedance $Z_L$ that is between 1.89 and 2.02 megrayls inclusive contained in said chamber so as to conduct acoustic waves from said transducer when coupled to said chamber to said diaphragm, the reflection coefficients $(Z_D - Z_L)/(Z_D + Z_L)$ and $(Z_B - Z_D)/(Z_B + Z_D)$ and the thickness of the diaphragm being such that the acoustic waves from said transducer that are reflected at the outer and inner surfaces of said diaphragm cancel each other to such an extent that the energy reflected toward the transducer is within 6 db of the energy reflected from these surfaces when the reflection coefficients are equal and the thickness of the diaphragm is precisely an odd number of quarter-wavelengths of the central frequency of the transducer with which the stand-off device is to be used.

2. A stand-off device set forth in claim 1 wherein said liquid includes thallous format.

3. A stand-off device as set forth in claim 1 wherein said liquid includes iodoform.

4. A stand-off device as set forth in claim 1 wherein said liquid includes cesium sulfate.

* * * * *